United States Patent [19]

Chen et al.

[11] Patent Number: 5,426,250
[45] Date of Patent: Jun. 20, 1995

[54] PROCESS FOR PREPARING 1,4-BUTANEDIOL

[75] Inventors: Shien C. Chen, Taipei; Cheng C. Chu, Kaohsiung; Fu S. Lin, Kaohsiung; June Y. Chou, Kaohsiung, all of Taiwan, Prov. of China

[73] Assignee: Darien Chemical Corporation, Taipei, Taiwan, Prov. of China

[21] Appl. No.: 237,333

[22] Filed: May 3, 1994

Related U.S. Application Data

[63] Continuation of Ser. No. 2,949, Jan. 11, 1993, abandoned.

[51] Int. Cl.⁶ ............................................. C07C 27/04
[52] U.S. Cl. .................................... 568/862; 568/877; 568/454
[58] Field of Search .................. 568/862, 867, 454

[56] References Cited

U.S. PATENT DOCUMENTS 4,740,626  4/1988  Bahrmann et al. .............. 568/454

FOREIGN PATENT DOCUMENTS 1085940  3/1989  Japan .

OTHER PUBLICATIONS

Copelin, Preparation of diols from unsaturated alcohols, 904 OG 274, Nov. 21, 1972.

Primary Examiner—Howard T. Mars
Assistant Examiner—Rebecca Cook
Attorney, Agent, or Firm—Birch, Stewart, Kolasch & Birch

[57] ABSTRACT

1,4-butanediol is prepared from allyl alcohol containing allyl acetate and water. The allyl alcohol is subjected to a hydroformylation reaction in the presence of an organic solvent, a rhodium complex, and a phosphorous compound under an atmosphere of carbon monoxide and hydrogen, to produce a hydroformylation product, which is extracted with an alkaline aqueous solution in the presence of carbon monoxide and/or hydrogen. After the extraction, an extracted raffinate solution containing the rhodium complex in the organic solvent is recycled through the same hydroformylation process, while the extracted aqueous solution containing the hydroformylation product is subjected to a hydrogenation reaction in the presence of hydrogen, with a hydrogenation catalyst added, to produce 1,4-butanediol.

3 Claims, No Drawings

PROCESS FOR PREPARING 1,4-BUTANEDIOL

This application is a continuation of U.S. Ser. No. 08/002,949, filed Jan. 11, 1993, abandoned.

BACKGROUND OF THE INVENTION 1,4-Butanediol is an important raw material in the chemical industrial field. It is used in the preparation of highly valuable products, such as: polybutylene terephthalate (PBT), polyurethane (PU), tetrahydrofuran (THF), and γ-butyrolactone. Traditionally, 1,4-butanediol is prepared from acetylene and formaldehyde by the Reppe process. However, as acetylene has limited availability and has recently become expensive, processes for preparing 1,4-butanediol from other resources besides acetylene are gaining importance.

Among various processes for making 1,4-butanediol from other than acetylene, a process in which allyl alcohol is used as a starting material has the best potential for development. The process comprises the steps of subjecting allyl alcohol to a hydroformylation reaction in the presence of carbon monoxide and hydrogen to generate an intermediate 4-hydroxy-butanal, followed by a hydrogenation step to produce 1,4-butanediol. The reaction scheme is as follows.

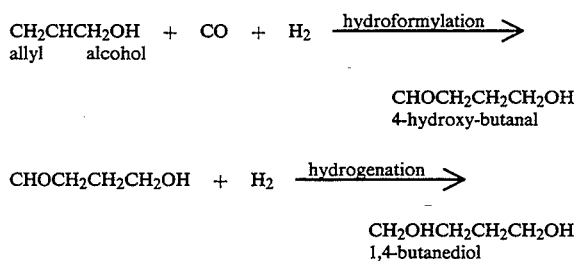

The study of the process of allyl alcohol hydroformylation was first reported by H. Adkins and G. Kresek [J. Amer. Chem. Soc., 78,388 (1948), and ibid., 79,3051 (1949)], wherein tetracarbonyl hydrido cobalt was used as a hydroformylation catalyst. However, it had a low reactivity and thus the reaction required a high temperature and a high pressure to proceed. Furthermore, both the yield and selectivity of 4-hydroxy-butanal were very low in that system. Later, C. K. Brown and G. Wilkinson [Tetrahedron Letters, 22,1725 (1969) and J. Chem. Soc. (A) 2753 (1970)] and B. Fell and M. Barl [Chemiker Zeitung, 101,343 (1977)] followed H. Adkins and G. Kresek's method, except that hydrido carbonyl tris(triphenyl phosphine) rhodium and tertiary phosphine ligands were used as catalysts to increase the reaction rate by 100 to 1000 times, and as a result the yield and selectivity were greatly improved. The above method proposed by Brown et al. seemed to be commercially more practical.

However, allyl alcohol is still not a chemical substance that is available on a bulk commercial scale. Thus, in order to produce 1,4-butanediol from allyl alcohol commercially, a steady supply of allyl alcohol, at a low cost, is necessary. Currently, the following three typical methods are commonly used for the preparation of allyl alcohol:

a) isomerization of propylene oxide:

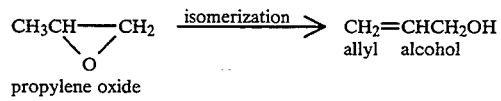

b) hydroxylation of allyl chloride:

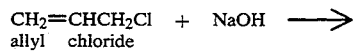

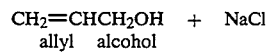

c) hydrogenation of acrolein:

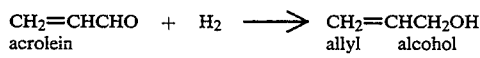

However, allyl alcohol produced with the above methods is still too costly for use in making 1,4-butanediol on an industrial scale. Recently, a process for preparing allyl alcohol at a higher yield and at a lower cost has been developed. As such, processes for preparing 1,4-butanediol from allyl alcohol have become more competitive. The referred to process for preparing allyl alcohol comprises the steps of subjecting a mixture of propylene, acetic acid, and oxygen to acetoxylation to produce allyl acetate and water, and hydrolyzing the allyl acetate to produce allyl alcohol the chemical reactions are shown in the following schemes:

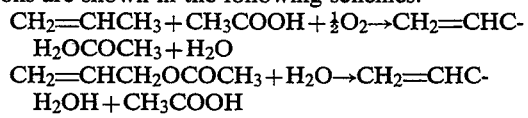

The allyl alcohol prepared from the above process is in an azeotropic mixture which contains about 30% $H_2O$ and a small amount of allyl acetate. As a result, it is therefore difficult to separate allyl alcohol from the mixture. Moreover, purification of allyl alcohol from the mixture increases the cost of producing 1,4-butanediol when pure allyl alcohol is needed as a starting material.

There are several inventions in the field. Kuraray company in Japanese Patent Publication Sho 51-29412 (1976) disclosed a process for preparing 1,4-butanediol from pure allyl alcohol which comprises the steps of subjecting pure allyl alcohol, carbon monoxide, and hydrogen to a hydroformylation reaction in a solvent containing a catalyst of rhodium carbonyl complex; extracting the reaction mixture with water; separating the solution into an organic phase containing catalyst and an aqueous phase containing aldehyde; recovering the organic phase and recycling it back to the hydroformylation system; and reacting the aqueous phase with hydrogen to produce 1,4-butanediol.

The distinctive feature of the process of Sho 51-29412 is in the process of extracting the hydroformylation product with water and separating the catalysts from the reaction mixture after hydroformylation. This process avoids the formation of high-boiling-point compounds from aldehydes during distillation processes for separating hydroformylation products currently used in the chemical industry (J. Falbe ed., "New Syntheses with carbon monoxide", Springer Venlya, 1980, p.171-). The accumulation of such high-boiling-point compounds in the reaction system would otherwise deteriorate the activities of the catalysts. Furthermore, the high temperature in the distillation process itself can also deactivate the catalyst. Thus, the process of Sho 51-29412 disclosed by Kuraray company prevents the above discussed disadvantages of the distillation.

Although the Kuraray process has advantages, it is only applicable to systems in which pure allyl alcohol is used as a feed stock.

As earlier mentioned it is costly to use purified allyl alcohol made from allyl acetate. On the other hand, if the mixture of allyl acetate, water and allyl alcohol is used as a feed stock in hydroformylation, the catalyst can suffer from deactivation (see Japanese Patent Kokai Sho 50-30809, and Japanese Patent Publication Sho 57-25018). Thus, Kuraray further proposed an improved process for preparing 1,4-butanediol from allyl alcohol containing allyl acetate as the starting material, which process was disclosed in Japanese Patent Publication Sho. 57-25018.

The process of Sho 57-25018 comprises extracting the hydroformylation product with water; contacting a portion of the hydroformylation catalyst solution with an alkaline aqueous solution; and recycling the catalyst solution through the hydroformylation system. In Sho 57-25018, it was indicated that the activity of the catalyst was stabilized, but after a thorough study by the inventors of the present Application, it has been found that the process of Sho 57-25018 may have solved some of the old problems encountered in the art but still left other problems to be solved (details will be discussed hereinafter). Further, it has been found that the process proposed by Sho 57-25018 was not the most desirable.

After intensive investigation by the inventors of the present invention, it has been found that the deactivation of the catalyst in the hydroformylation of allyl alcohol feed stock that contains allyl acetate and water can be attributed to the presence of an acid compound. The process disclosed in Japanese Patent Publication Sho 57-25018 solved the problem of hydroformylation catalyst deactivation. However, that process requires two extraction operations after the hydroformylation. In the first extraction by water, the aqueous phase contains an acid compound which causes a contamination and a generation of high-boiling-point materials in the successive hydrogenation reaction process. In the second extraction with alkaline aqueous solution a waste water is generated. Thus, the process needs further improvement.

SUMMARY OF THE INVENTION

The present invention provides improvements over the problems encountered in the preparation of 1,4-butanediol by hydroformylation of allyl alcohol that contains allyl acetate and water. The novel features of the present invention comprise an extraction of the hydroformylation product with an alkaline aqueous solution after the hydroformylation reaction, a recycling of the extracted residual solution that contains a rhodium catalyst to the hydroformylation system, and adding a hydrogenation catalyst to the extract to carry out the hydrogenation reaction in the presence of hydrogen to produce 1,4-butanediol. Accordingly, the present invention not only solves those problems existing in prior processes (e.g., Kuraray's processes), but also simplifies the operations needed in the entire process.

In summary, the present invention is an improved process for preparing 1,4-butanediol and comprises hydroformylating allyl alcohol (produced from allyl acetate), in an organic solvent, in the presence of a rhodium complex and a phosphorous compound and under an atmosphere containing carbon monoxide and hydrogen; extracting the hydroformylation product with an alkaline aqueous solution in the presence of carbon monoxide or hydrogen or both; recycling the extracted residual solution that contains the rhodium complex to the hydroformylation system; and adding a hydrogenation catalyst to the extract to carry out a hydrogenation reaction in the presence of hydrogen gas to produce 1,4-butanediol. In the process, the allyl alcohol which is used as a starting material contains allyl acetate and water.

DETAILED DESCRIPTION OF THE INVENTION

The hydroformylation catalysts employed in the present invention include rhodium complex and ligands of phosphorous compounds. Examples of said rhodium complex include: hydrido carbonyl tris(triphenyl phosphine) rhodium, chloro carbonyl bis(triphenyl phosphine) rhodium, and acetylacetonato carbonyl(triphenyl phosphine) rhodium. These rhodium complexes are highly active and are effective as catalysts under low temperature, low pressure, and low concentration. In the hydroformylation reaction, besides 4-hydroxy butanal, its isomer 2-methyl-3-hydroxypropanal is also generated. In order to reduce production of the isomer and to maintain activity of the catalyst, ligands of phosphorous compounds are added. Examples of these compounds include: mono tertiary-phosphine compounds, such as triphenyl phosphine, para-bromophenyl diphenyl phosphine, butoxy diphenyl phosphine, n-butyl diphenyl phosphine, t-butyl diphenyl phosphine, cyclohexyl diphenyl phosphine, di-n-butyl phenyl phosphine, ethyl diphenyl phosphine, heptyl diphenyl phosphine, hexyl diphenyl phosphine, methyl diphenyl phosphine, isopropyl diphenyl phosphine, ortho-toly diphenyl phosphine, paramethyl diphenyl phosphine, tri-isobutyl phosphine, tri-n-butyl phosphine, etc., bis tertiary-phosphine compounds such as 1,4-bis(diphenyl phosphino)butane, 1,3-bis(diphenyl phosphine)propane, 1,2-bis(-diphenyl phosphine)ethane, 2,3-0-isopropylidene-2,3-dihydroxy-1,4-bis(diphenyl phosphino)butane, trans-1,2-bis(diphenyl phosphine methyl)cyclobutane, etc.; or ferrocene compounds such as 1,1-bis(diphenyl phosphino)ferrocene. Generally, the rhodium complex is used in an amount such that the rhodium atom concentration ranges from 0.5 mM to 20 mM, and preferably from 1 mM to 10 mM, and the mole ratio between the phosphorous compound and rhodium complex is about (3 to 1000) to 1, and preferably (30 to 350) to 1.

The solvent used in the hydroformylation reaction must be capable of dissolving the catalysts and have low compatibility with water, and therefore aromatic compounds are preferable, such as benzene, toluene, xylene, mesitylene, chlorobenzene, bromobenzene, dichlorobenzene, chlorotoluene, and bromotoluene. The amount of the solvent used is 1 to 15 times that of the feed stock of allyl alcohol by weight.

Because the present invention involves a novel extraction operation, the allyl alcohol hydroformylation feed stock used can be a crude allyl alcohol product made from allyl acetate, and which feed stock may contain allyl acetate and water. As such, this invention provides a method of preparing 1,4-butanediol without the need of an allyl alcohol purification process and therefore is lower in cost and offers a higher competitiveness in commercial scale operations.

The rate and selectivity of the hydroformylation reaction are influenced by pressure, temperature, and the mole ratio of hydrogen to carbon monoxide. In the present invention, the reaction pressure can range from atmospheric pressure to 100 kg/cm$^2$, and preferably from 3 to 15 kg/cm$^2$; the temperature can range from 30 to 150° C., and preferably from 50° to 100° C.; the mole ratio of hydrogen to carbon monoxide can range from 1:10 to 10:1 and preferably from 1.2 to 3:1.

In the present invention, the extraction of the hydroformylation product with alkaline aqueous solutions after completion of the hydroformylation reaction is carried out in the presence of carbon monoxide, hydrogen, or both. This not only extracts out the hydroformylation product but also reduces the amount of acid in the resulting catalyst containing organic phase. In order to minimize the generation of a high-boiling-point compound and other impurities that are difficult to remove after the hydrogenation of the extract, the pH value of the alkaline aqueous solution is adjusted so that the pH value of the aqueous extract ranges from 5 to 9. The alkaline aqueous solution is made by dissolving compounds such as hydroxides, carbonates, and acetates in pure water. In addition, the amount of the alkaline aqueous solution to be used needs to be finely controlled. An inappropriate amount of the aqueous solution will not provide a desired extraction efficiency. Moreover, too high a concentration of the hydroformylation product in the aqueous extract will cause an increase in the generation of by-products formed during the hydrogenation reaction. The increase in by-products results in a reduced yield of 1,4-butanediol. Therefore, there is a minimum amount of aqueous solution required for extraction. On the other hand, if too much extracting solvent is used, the hydroformylation product concentration will be too low, and thus the next hydrogenation reaction rate will be low, and furthermore, the hydrogenation will require a reactor of a larger volume. Therefore, there is also a upper limit on the amount of the aqueous solution to be used for extraction. The preferable amount of extracting solution ranges from 1 to 20 times the allyl alcohol feed by weight.

As a hydrogenation catalyst for the hydrogenation reaction, the metal-supported catalysts, which are supported by such metals as rhodium, palladium, nickel, ruthenium, cobalt, and platinum can be used, and oxide catalysts such as rhenium oxide, cobalt oxide, and copper chromium oxide; or Raney nickel can also be used. Among them, a nickel or ruthenium supported catalyst, copper chromium oxide, and Raney nickel give better results. A suitable amount of hydrogenation catalyst to use can range from 5 to 40% of allyl alcohol feed stock by weight.

The hydrogenation reaction is carried out under a pressure of from 10 to 100 kg/cm$^2$; and preferably from 20 to 60 kg/cm$^2$, and at a reaction temperature ranging from 50° to 200° C., and preferably from 70° to 130° C.

The present invention can be better illustrated by, but not limited to, the following examples.

EXAMPLE 1

Carbonyl hydrido tris(triphenyl phosphine) rhodium 0.184 g, triphenyl phosphine 7.711 g, allyl alcohol 21.25 g, water 2.360 g and mesitylene 86.37 g were charged into a jacketed stirred stainless steel reactor (a first reactor). The temperature inside the reactor was controlled at 68° C. and the pressure was kept at 4.4 kg/cm$^2$ G under hydrogen and carbon monoxide (mole ratio 1.2:1) to carry out a hydroformylation reaction for 3.5 hours. The conversion of allyl alcohol was 99%.

The reaction mixture, in the presence of hydrogen and carbon monoxide (mole ratio 1), was extracted with 93.4 ml of water to separate into two layers. The upper mesitylene phase, which was thus recovered, containing hydroformylation catalyst was subjected to a second hydroformylation reaction in the same first hydroformylation reactor. The bottom aqueous phase was charged into another (a second) jacketed stirred stainless steel reactor (the hydrogenation reactor), and 5.000 g of hydrogenation catalyst (Ni-3266p of Harshaw/Filtrol, U.S.A.) was added to carry out a hydrogenation reaction. Inside the second reactor the temperature was controlled at 86° C. and the pressure at 80 kg/cm$^2$ G under hydrogen gas. After reacting for 8 hr., 1,4-butanediol 24.006 g, 2-methyl-1,3-propanediol 6.398 g, and propanol 0.721 g were obtained.

To the above mentioned recovered solution that contained hydroformylation catalyst were added allyl alcohol 21.250 g, water 2.360 g, and allyl acetate 0.333 g to carry out another hydroformylation reaction. At this time, the temperature inside the first reactor was controlled at 68° C., and the pressure at 4.4 kg/cm$^2$ under hydrogen and carbon monoxide (mole ration 1.2:1) to reaction for 3.5 hours. The allyl alcohol conversion was only 42%.

The reaction solution was then extracted with 93.4 ml of sodium hydroxide solution (pH 12.5) in the presence of hydrogen and carbon monoxide (mole ratio 1). After the phase separation, an upper layer of hydroformylation catalyst solution in mesitylene and a bottom layer of aqueous hydroformylation product solution of pH 8.6 were obtained. The upper layer was subjected to still another (third) hydroformylation reaction in the same reactor (the first reactor).

In the above mentioned third successive hydroformylation reaction, allyl alcohol 21.250 g and water 2.360 g were added to carry out the same hydroformylation reaction. The temperature was controlled at 68° C. and pressure at 4.4 kg/cm$^2$ G under hydrogen and carbon monoxide (mole ratio 1.2:1). After a 3.5 hr reaction, the allyl alcohol conversion was 99%.

The reaction solution was extracted with 93.44 ml of water in the presence of hydrogen and carbon monoxide (mole ratio 1). The bottom layer was charged into the hydrogenation reactor (the second reactor) with 5.032 g of hydrogenation catalyst added to carry out the same hydrogenation reaction. The temperature was controlled at 86° and a pressure of 80 kg/cm$^2$ G under hydrogen. After reacting for 8 hr., 23.764 g of 1,4-butanediol, 6.270 g of 2-methyl-1,3-propanediol, and 0.731 g of propanol were obtained.

COMPARATIVE EXAMPLE 1

The reaction was carried out following the same procedures as in Example 1, except the extraction of the hydroformylation reaction solution with a pH 12.5 sodium hydroxide solution was done under an atmosphere of open air. The recovered catalyst solution was used in the next cycle of hydroformylation. After a 3.5 hr. reaction, the conversion of allyl alcohol was only 9%.

EXAMPLE 2

The same was done as in Example 1 except that extraction of the hydroformylation reaction solution with a pH 12.5 sodium hydroxide aqueous solution was carried out in the presence of hydrogen. The recovered catalyst solution was used in the next hydroformylation reaction. After a 3.5 hr. reaction, the allyl alcohol conversion was 99%.

EXAMPLE 3

Carbonyl hydrido tris(triphenyl phosphine) rhodium 0.514 g, triphenyl phosphine 1.322 g, 2,3-O-isopropylidene-2,3-dihydroxy-1,4-bis(diphenyl phosphino)butane 1.255 g, allyl alcohol 21.250 g, water 2.500 g, allyl acetate 0.184 g and benzene 87.800 g were charged into a jacketed stirred stainless steel reactor. The reaction temperature was controlled at 70° C., and the pressure was controlled at 5 kg/cm$^2$ G under hydrogen and carbon monoxide (mole ratio 1.5) to carry out a hydroformylation reaction for 3.5 hour. The allyl alcohol conversion was 64%.

The reaction solution was extracted with 110 ml of potassium hydroxide (pH 12.2) solution in the presence of hydrogen and carbon monoxide (mole ratio 1). After the phase separation, an upper layer of benzene solution containing hydroformylation catalyst and a bottom aqueous layer of pH 7.7 containing the hydroformylation product were obtained. The upper layer thus recovered was subjected to the same hydroformylation reaction.

To the hydroformylation reactor with the recovered catalyst solution, allyl alcohol 21.250 g and water 2.500 g were added to carry out a hydroformylation reaction. The temperature was controlled at 70° C. and the pressure was controlled at 5 kg/cm$^2$ G under hydrogen and carbon monoxide (mole ration 1.5). After a 3.5 hour reaction, the allyl alcohol conversion was 99%.

The reaction solution was extracted with 110 ml of water in the presence of hydrogen and carbon monoxide (mole ratio 1). The bottom layer was charged into a hydrogenation reactor to which 5.621 g of hydrogenation catalyst (Hoechst RCH Nickel 52/53) was added to carry out a hydrogenation reaction. The temperature was controlled at 85° C. and the pressure at 80 kg/cm$^2$ G under hydrogen. After an 8 hr. reaction, 1,4-butanediol 25.512 g, 2-methyl-1,3-propanediol 3.071 g and propanol 1.792 g were obtained.

EXAMPLE 4

Continuous hydroformylation and extraction were carried out in a jacketed stirred stainless steel reactor and a packed bed tower extractor, respectively. The conditions of the hydroformylation reaction were: carbonyl hydrido tris(triphenyl phosphine) rhodium concentration 2 mmole/liter, triphenyl phosphine concentration 320 mole/liter, catalyst solution average residence time 3.5 hr, feed of allyl alcohol (containing 10 wt % water and 0.004 wt % allyl acetate) 52.2 g/hr, reaction temperature 65° C., pressure 4.2 kg/cm$^2$ G, mole ratio of hydrogen to carbon monoxide 1. The conditions of extraction were water pumping rate 468 ml/hr, hydroformylation reaction solution feed 310 ml/hr, with the extraction tower sealed with hydrogen and carbon monoxide.

In the first 5 days after the reaction was started, the average allyl alcohol conversion was 92%. The aqueous extract was hydrogenated in the presence of Harshaw/-Filtrol Ni-3266p hydrogenation catalyst in a hydrogenation reactor to give a 1,4-butanediol selectivity 66.1%, 2-methyl-propanediol selectivity 30.2%, and propanol selectivity 2.2%.

After 25 days continuous operation, allyl alcohol conversion decreased to 67%. Sodium hydroxide solution instead of water was used to extract hydroformylation product in the extraction tower, and was pumped in at a rate of 310 ml/hr. The pH of the sodium hydroxide solution was adjusted between 9.5 and 11.5 to keep the pH of the extract between 5 and 9. After five more days of operation, allyl alcohol conversion was 93% and after hydrogenation of the extract (aqueous phase), 1.4-butanediol of selectivity 66.6%, 2-methyl-propanediol of selectivity 30.8%, and propanol of selectivity 2.2% were obtained.

EXAMPLE 5

Continuous hydroformylation and extraction were carried out in a jacketed stirred stainless steel reactor and a packed bed tower extractor, respectively. The reaction conditions of the hydroformylation reaction were: carbonyl hydrido tris(triphenyl phosphine) rhodium concentration 2 mmole/liter, triphenyl phosphine concentration 320 mmole/liter, average catalyst solution average residence time 3.5 hr, allyl alcohol feed (containing 11 wt % water and allyl acetate 0.009 wt %) 52.6 g/hr, reaction temperature 65° C., reaction pressure 4.2 kg/cm$^2$ G, and mole ratio between hydrogen and carbon monoxide 1. The conditions of extraction tower were: extracting agent feed pumping rate 465 ml/hr, hydroformylation reaction solution feed rate 312 ml/hr, and sealed with hydrogen and carbon monoxide. The pH of the sodium hydroxide solution was adjusted between 9 and 11 to keep the pH of the extract between 5 and 9.

In the first 5 days after the reaction was started, the average allyl alcohol conversion was 93%. After hydrogenation of the extract (aqueous phase) 1.4-butanediol of selectivity 66.6%, 2-methyl-propanediol selectivity 30.8%, and propanol selectivity 2.2%.

After 25 days continuous operation, the allyl alcohol conversion was 93% and the selectivities of hydrogenation products of the extract were same as those obtained after 5 days operation. 2.2% were obtained.

After 25 days continuous operation, the allyl alcohol conversion was 93% and the selectivities of hydrogenation products of the extract were same as those obtained after 5 days operation.

What we claim is:

1. A method for preparing 1,4-butanediol, comprising the steps of:
   hydroformylating an allyl alcohol feed stock in a hydroformylating system, wherein the hydroformylating occurs in an organic solvent and under an atmosphere consisting essentially of carbon monoxide and hydrogen in a mole ratio of hydrogen to carbon monoxide of 1:10 to 10:1, under a pressure of 1 kg/cm$_2$ to 100 kg/cm$_2$ and a temperature of 30° to 150° C., in the presence of a rhodium complex and a phosphorus compound having a mole ratio of about 3:1 to about 1000:1, to thereby obtain a hydroformylation product in the organic solvent,
   wherein the organic solvent has a low compatibility with water, is capable of dissolving said rhodium complex and phosphorous compound and the amount of which is 1 to 15 times that of the feed stock of allyl alcohol by weight, and the allyl alcohol feed stock is prepared from allyl acetate and contains allyl acetate and water as impurities therein;
   extracting said hydroformylation product from the organic solvent with an alkaline aqueous solution which is present in an amount of from 1 to 20 times by weight of the amount of the allyl alcohol feed stock, in the presence of at least one gaseous substance selected from the group consisting of carbon monoxide and hydrogen to give an aqueous extract solution having a pH of from 6 to 8.6 and containing the hydroformylation product;

recovering as an extracted raffinate phase solution, the organic solvent containing the rhodium complex and the phosphorous compound and recycling the rhodium complex and the phosphorous compound to the hydroformylation system; and hydrogenating the aqueous extract solution with a hydrogenation catalyst in the presence of hydrogen, under a pressure of 10 to 100 kg/$cm_2$ and a temperature of 50° to 200° C., to obtain 1,4-butanediol.

2. A method for preparing 1,4-butanediol, comprising the steps of:

hydroformylating an allyl alcohol feed stock in a hydroformylating system, wherein the hydroformylating occurs in an organic solvent and under an atmosphere consisting essentially of carbon monoxide and hydrogen in a mole ratio of hydrogen to carbon monoxide of 1:10 to 10:1, under a pressure of 1 kg/$cm_2$ to 100 kg/$cm_2$ and a temperature of 30° to 150° C., in the presence of a rhodium complex and a phosphorus compound having a mole ratio of about 3:1 to about 1000:1, to thereby obtain a hydroformylation product in the organic solvent, wherein the organic solvent has a low compatibility with water, is capable of dissolving said rhodium complex and phosphorous compound and the amount of which is 1 to 15 times that of the feed stock of allyl alcohol by weight, and the allyl alcohol feed stock is prepared from allyl acetate and contains allyl acetate and water as impurities therein;

extracting said hydroformylation product from the organic solvent with an alkaline aqueous solution which is present in an amount of from 1 to 20 times by weight of the amount of the allyl alcohol feed stock, in the presence of at least one gaseous substance selected from the group consisting of carbon monoxide and hydrogen to give an aqueous extract solution having a pH of from 5 to 8.6 and containing the hydroformylation product;

recovering as an extracted raffinate phase solution, the organic solvent containing the rhodium complex and the phosphorous compound and recycling the rhodium complex and the phosphorous compound to the hydroformylation system; and hydrogenating the aqueous extract solution with a hydrogenation catalyst in the presence of hydrogen, under a pressure of 10 to 100 kg/$cm_2$ and a temperature of 50° to 200° C., to obtain 1,4-butanediol.

3. A method for preparing 1,4-butanediol, comprising the steps of:

hydroformylating an allyl alcohol feed stock in a hydroformylating system, wherein the hydroformylating occurs in an organic solvent and under an atmosphere consisting essentially of carbon monoxide and hydrogen in a mole ratio of hydrogen to carbon monoxide of 1:10 to 10:1, under a pressure of 1 kg/$cm_2$ to 100 kg/$cm_2$ and a temperature of 30° to 150° C., in the presence of a rhodium complex and a phosphorus compound having a mole ratio of about 3:1 to about 1000:1, to thereby obtain a hydroformylation product in the organic solvent, wherein the organic solvent has a low compatibility with water, is capable of dissolving said rhodium complex and phosphorous compound and the amount of which is 1 to 15 times that of the feed stock allyl alcohol by weight, and the allyl alcohol feed stock is prepared from allyl acetate and contains allyl acetate and water as impurities therein;

extracting said hydroformylation product from the organic solvent with an alkaline aqueous solution which is present in an amount of from 1 to 20 times by weight of the amount of the allyl alcohol feed stock, in the presence of at least one gaseous substance selected from the group consisting of carbon monoxide and hydrogen to give an aqueous extract solution having a pH of from 5 to 7.7 and containing the hydroformylation product;

recovering as an extracted raffinate phase solution, the organic solvent containing the rhodium complex and the phosphorous compound and recycling the rhodium complex and the phosphorous compound to the hydroformylation system; and hydrogenating the aqueous extract solution with a hydrogenation catalyst in the presence of hydrogen, under a pressure of 10 to 100 kg/$cm_2$ and a temperature of 50° to 200° C., to obtain 1,4-butanediol.

* * * * *

UNITED STATES PATENT AND TRADEMARK OFFICE
CERTIFICATE OF CORRECTION

PATENT NO. : 5,426,250
DATED : June 20, 1995
INVENTOR(S) : Chen et al.

It is certified that error appears in the above-indentified patent and that said Letters Patent is hereby corrected as shown below:

Title page, item [73], Assignee: Change "Darien Chemical Corporation" to --Dairen Chemical Corporation--.

Claim 1, Line 12 (Col. 8, line 56), change "about 3:1 to about 1000:1," to --about 1:3 to about 1:1000,--

Claim 2, Line 12 (Col. 9, line 28), change "about 3:1 to about 1000:1," to --about 1:3 to about 1:1000,--

Claim 3, Line 12 (Col. 10, line 20), change "about 3:1 to about 1000:1," to --about 1:3 to about 1:1000,--

Signed and Sealed this

Twelfth Day of March, 1996

*Attest:*

BRUCE LEHMAN

*Attesting Officer*     Commissioner of Patents and Trademarks